United States Patent [19]

Kolff et al.

[11] Patent Number: 5,397,349
[45] Date of Patent: Mar. 14, 1995

[54] MUSCLE AND AIR POWERED LVAD

[75] Inventors: Willem J. Kolff; Stephen R. Topaz; N. Dan Bishop, all of Salt Lake City, Utah

[73] Assignee: University of Utah Research Foundation, Salt Lake City, Utah

[21] Appl. No.: 922,208

[22] Filed: Jul. 30, 1992

[51] Int. Cl.$^6$ ............................................. A61M 1/12
[52] U.S. Cl. ............................ 623/3; 600/18; 600/16; 623/26
[58] Field of Search .............................. 623/3, 25, 26; 600/16–18

[56] References Cited

U.S. PATENT DOCUMENTS

| 4,453,537 | 6/1984 | Spitzer | 623/3 |
| 4,652,265 | 3/1987 | McDougall | 623/3 |
| 4,693,714 | 9/1987 | Lundback | 623/3 |
| 4,968,293 | 11/1990 | Nelson | 600/16 |
| 4,979,936 | 12/1990 | Stephenson et al. | 600/16 |
| 5,273,518 | 12/1993 | Lee et al. | 600/16 |

OTHER PUBLICATIONS

Kusserow et al., "A Small Ventricle-Type Pump for Prolonged Perfusions", vol. X Trans. Amer. Soc. Artif. Int. Organs, 1964, pp. 74–78.

Ugolini, in Chiu, *Biomedical Cardiac Assist*, 1986, Ch. 14, pp. 193–210.

Muscle Powered Circulatory Assist Device for Diastolic Counterpulsator, Novoa, et al.

*Primary Examiner*—David H. Willse
*Attorney, Agent, or Firm*—Thorpe, North & Western

[57] ABSTRACT

A method for providing ventricular assist to a patient with a weak or nonfunctional heart includes attaching an artificial ventricle to a patient and pumping said artificial ventricle with a muscle powered hydraulic pump. This method is enhanced by supplementing said artificial ventricle as needed with a pneumatic pumping system which is hermetically sealed from the hydraulic fluid. The hydraulic pumping power is amplified by driving a first pumping member of larger dimension against a second pumping member of smaller dimension to thereby supply increased force to overcome existing blood pressure.

6 Claims, 6 Drawing Sheets

MUSCLE AND AIR POWERED LVAD

BACKGROUND OF THE INVENTION

1. Field of Invention

This invention relates to ventricle assist devices useful to aid or replace a damaged heart. More particularly, the present invention pertains to ventricle assist devices which utilize natural muscle tissue as a pumping source.

2. Prior Art

A major challenge in implementation of a convenient ventricular assist therapy remains the development of a power source which is self-sustaining and compact. Typical forms of pumping units include some variation of a mechanical drive unit which utilizes a piston, roller pump, axial impeller, or other mechanical structure for moving pumping fluid through a recirculating drive system. Such a pumping unit must be small in size, capable of alternating and reversible flow, operable on minimal power consumption, consistent and dependable. Without question, the difficulty of mechanically reproducing the simple pumping action of the human heart has been and remains formidable.

It has been well established that a fast-twitching skeletal muscle can be converted into a slow twitching continuous acting muscle, similar to a heart muscle, by chronic stimulation with bursts of electrical pulses. Myoplasty around the natural heart has been done clinically with apparent success in many institutions. Some efforts have also been made to apply skeletal muscle around a blood sac and to use the contraction of the muscle around the blood sac to expel the blood contents in a manner similar to the contraction of a cardiac muscle. The refill cycle occurs by flow under pressure within the vascular system. By attaching this pumping system to the aorta of a weak heart, the pumping action of the muscle powered ventricle assist device can increase circulation to a more effective level. Unfortunately, the pumping capacity of the muscle directly applied to the blood sac is not always sufficient to offer ventricular assist for general applications. Sometimes such a system does not have the power to provide ventricular assist to the left ventricle, which requires greater pumping pressure than the right ventricle.

In addition to these limitations, mortality has been high for patients using this procedure, perhaps in part because these techniques are only applied as a last resort. The myoplasty operation in sick patients requires six hours and requires training of the skeletal muscle for approximately six weeks. To reduce the high mortality rate, selection of patients in deep failure was excluded. Nevertheless, interest in cardiomyoplasty remains high world-wide. Accordingly, what is needed is a form of muscle activated pumping system which supplies greater pressure and which includes additional pumping backup and power source to complement the contraction power offered by the muscle tissue, particularly in the beginning.

OBJECTS AND SUMMARY OF THE INVENTION

It is an object of the present invention to provide a muscle powered ventricle assist device which can be coupled into the natural aorta, without requirement of valve or other flow control.

It is a further object of this invention to provide muscle powered ventricular assist to the aorta which includes means for amplifying the pressure output from the muscle contraction.

It is yet another object of this invention to provide a supplemental pumping source in combination with the muscle powered ventricle to generate additional pumping power, as well as provide a backup pumping source in the event of failure of the primary muscle powered pumping system.

These and other objects are realized in a ventricular assist device, comprising an artificial ventricle including a blood chamber and a drive chamber, in which the blood chamber and drive chamber are separated by at least one pumping member. The blood chamber includes conduit means for coupling the blood chamber to a patient's circulatory system to allow reciprocating blood flow between the blood chamber and the circulatory system. The drive chamber includes a first pumping fluid contained therein and an associated compressible means which enables an alternating reduction and expansion of an interior volume of the drive chamber to displace the pumping fluid against the pumping member and thereby pump blood contained within the blood chamber to assist blood flow within the circulatory system. This compressible means includes muscle tissue applied at an outer surface of and in circumscribing relation around the compressible means and is responsive to be reduced in size by contraction of the muscle tissue and to supply a drive force to the first pumping fluid. Actuating means is coupled to the muscle tissue to periodically contract and release the muscle tissue in a pattern which is compatible with the patient's heartbeat. The muscle pumping force may be amplified by resisting the first pumping fluid with a large pumping member or membrane, and then applying that pumping force to a smaller pumping member which is coupled to the blood compartment.

Other objects and features of the present invention will be apparent to those skilled in the art, based on the following detailed description, taken in combination with the accompanying drawings. For example, the pressure amplification device described in principle only can be incorporated within the pouch which can be either surrounded by skeletal muscle or put between the skeletal muscle and the rib cage.

DETAILED DESCRIPTION OF THE INVENTION

Figure 1:
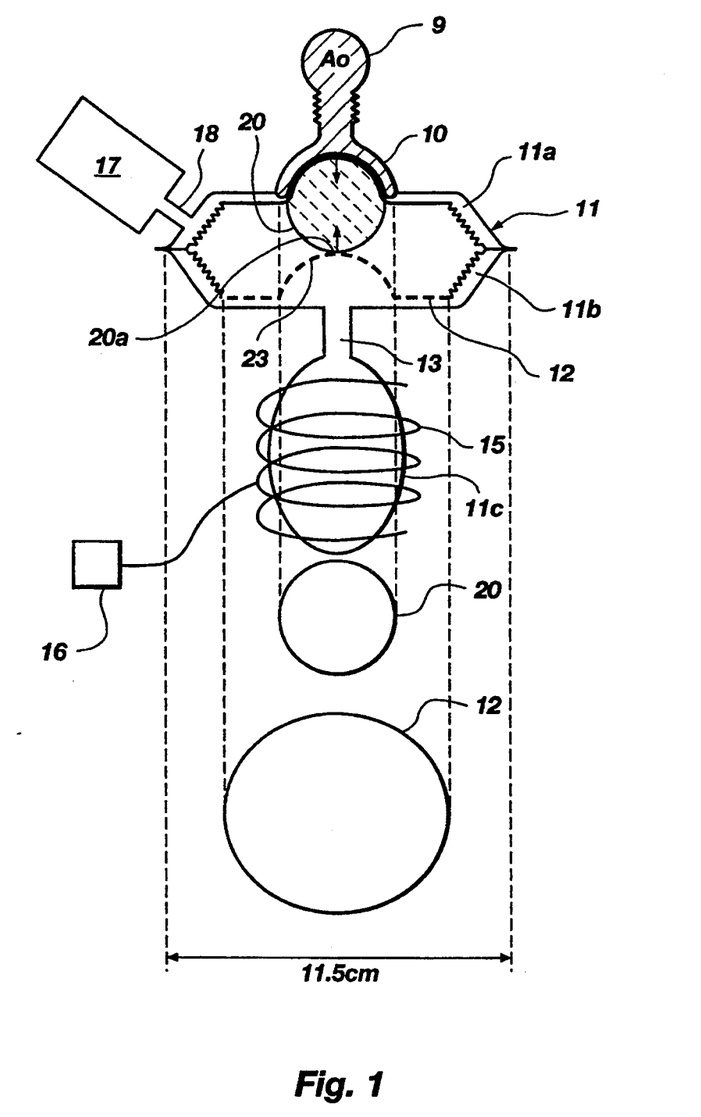
FIG. 1 graphically depicts a muscle powered ventricular assist device which includes means for supplementing pumping forces to complement the muscle powered pumping forces.

Referring now to the drawings:

FIG. 1 shows a preferred embodiment of the present invention which can be attached to an aorta as part of a left ventricular assist device. This includes an artificial ventricle including a blood chamber 10, which is to be coupled to the aorta 9 of a patient. The blood chamber 10 is in the form of a flexible, collapsible blood sac which is fabricated in accordance with well known principles that need not be detailed in this disclosure and is shown in systolic mode. The blood chamber is spherical in its expanded or diastolic mode and operates in conjunction with a pumping chamber 11. This pumping chamber comprises a first chamber 11b and 11c which contains a pumping fluid (carbon dioxide or saline) for displacing the pumping membrane 12. A second pumping chamber 11a is provided to assist this pumping membrane 12, and is discussed hereafter. Pumping chamber 11b includes a connecting conduit 13 which is coupled to a compressible portion 11c which is wrapped with a muscle 15 such as a latissimus dorsi muscle. It will be apparent to those skilled in the art that configurations for the blood chamber and drive chamber may differ; however, they will generally be separated by at least one pumping member 12.

The compressible chamber 11c or means is formed of pliable material that readily deforms under the constriction of the muscle. It contains the bulk of pumping or drive fluid. The chamber shown in FIG. 1 is ellipsoidal; however, other configurations may be adopted as represented in the other figures. Indeed, the pressure amplifying device can be reduced in size and have such configuration that it can be either surrounded by skeletal muscle or can be put between the muscle and the rib cage. A linear actuator connected to the end or tendon of the muscle can also be used. The muscle tissue is applied at an outer surface of and in circumscribing relation around the compressible chamber so that the chamber is responsive to being reduced in size by contraction of the muscle tissue. The resultant drive force is applied to the contained drive fluid (also referred to as the first pumping fluid). The interconnecting conduit 13 needs to have a sufficiently large flow diameter to minimize channel resistance to transfer of the drive fluid.

Some form of electrical stimulation or actuating means 16 must be coupled to the muscle tissue to periodically contract and release the muscle tissue in a pattern which is compatible with the patient's heartbeat. These devices are commercially available and have been refined to provide a dependable source of regulation for muscle contraction.

A significant feature of the present invention is the addition of a second pumping means 17, which is mechanically driven in contrast to being muscle driven, and a conduit 18 coupled between the second pumping means and the drive chamber 11a for transfer of pumping fluid to and from the drive chamber. This provides a pumping force in counterpulsation to the drive force applied by the muscle tissue. For example, as a positive drive force is applied from the contraction of the muscle 15 which pushes the pumping membrane or member 12 forward, collapsing the blood sac 10, a negative pressure is produced within the second pumping means 17. This tends to draw the pumping member 12 forward with greater force, providing a complementary pumping effort.

In this preferred embodiment, this dual pumping system is implemented with the second part 11a of the drive chamber 11 which is at least partially formed between (i) a first pumping member 12 which is displaced directly by the drive fluid and force of muscle contraction and (ii) a second pumping member 20 associated with the blood chamber. In this case, the second pumping member actually forms part of the flexible housing for the blood chamber. As indicated previously, the first pumping member 12 also extends and retracts in response to negative and positive pressures respectively generated by the second pumping means 17. The second pumping means comprises a pneumatic pump which pumps the gas in counterpulse manner with respect to the drive chamber when the muscle tissue provides insufficient drive force to provide adequate cardiac output.

It should be noted that the size of the first pumping member 12 is substantially larger than the second pumping member 20. This structure differential provides an amplifying effect, converting the lesser pressure of the initial muscle contraction to a significantly increased pressure output because of the smaller size of the second pumping member 20. Specifically, the first pumping member 12 has a relatively large surface area subject to direct displacement by the drive fluid powered by the muscle tissue, as compared with the second pumping member 20 which has a relatively smaller surface area which applies force directly at the blood chamber. This corresponds to a linear conversion of force similar to geared transmissions which provide changes in power transmission. This can be accomplished by numerous configurations. Generally, the first pumping member 12 will have a diameter of up to approximately twice the diameter of the second pumping member 20 and will be operable to be displaced by direct movement of the first pumping member. For example, the diameter of the first pumping member 12 is 8.1 cm, whereas the diameter of the second pumping member 20 is 6.4 cm.

In the disclosed embodiments, the first pumping member 12 comprises a rigid pressure plate shaped as a disk with a central dome section 23. The disk and dome are collectively displaced by the drive fluid and contraction of the muscle tissue 15. This plate is rigid so that force applied by contraction of the muscle displaces the total disk 12. In other words, displacement of the total rigid area of the large disk receives the full applied force, which is then focused into the second pumping member 20 as the small leading edge 23a of the central dome section 23 encounters the filled blood chamber at its lower spherical surface 20a. By imposing the applied force from the larger compartment of the pumping chamber into the smaller compartment of the blood chamber, pressure amplification occurs. This provides the higher level of pressure required to displace blood from the blood chamber, whereas the contraction of the wrapped muscle by itself may not generate a strong enough pressure to reach the required blood pressure level.

The dome configuration is obviously only one of numerous structures that can be applied to develop this linear amplification of pressure. Typically, in each of these configurations will the first pumping member will be formed as a disk and include a central section which projects forward with a lesser diameter than the diameter of the disk The second pumping member should be positioned in alignment with the central section of the disk such that forward displacement of the disk results in contact by the central section with the second pumping member, thereby applying a forward, pumping force to the second pumping member. It is also possible to place the smaller, second member in a levered, off-center arrangement to further enhance power transfer.

Figure 2:
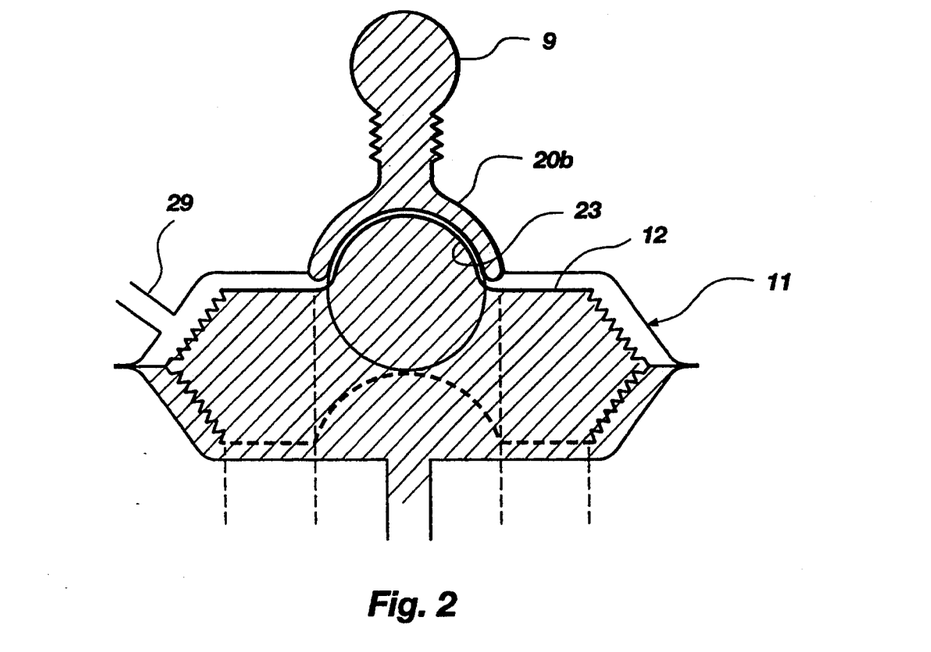
FIG. 2 graphically shows the assist device of FIG. 1 with the pumping components in a configuration corresponding to diastole.
Figure 3:
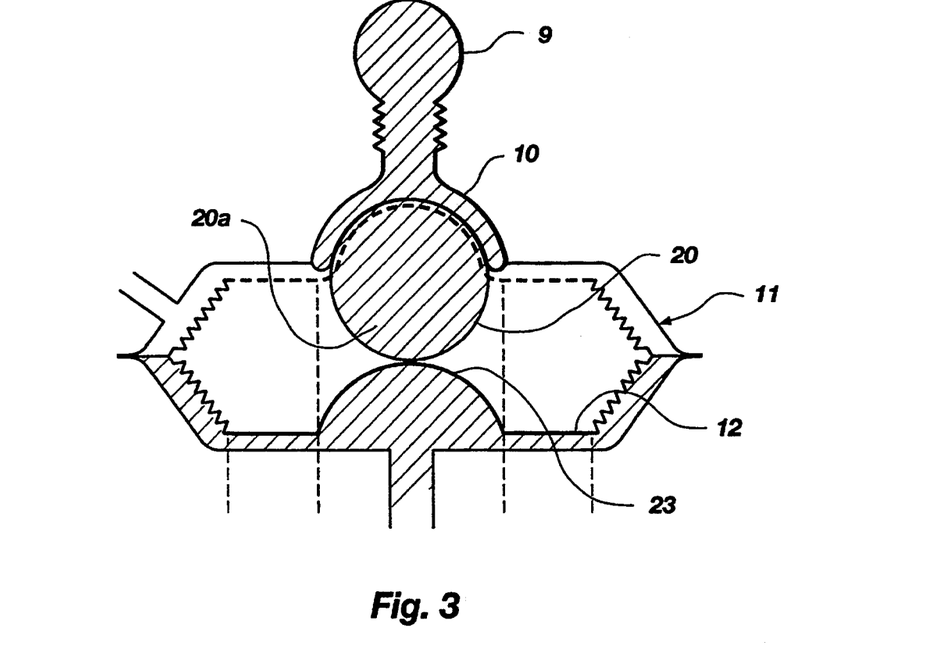
FIG. 3 graphically shows the assist device of FIG. 1 with the pumping components in a configuration corresponding to systole.

FIGS. 2 and 3 illustrate the specific action of the first pumping member 12 on the second pumping member 20, in which the collapsible dome configuration of the second pumping member forms part of the blood chamber. In this embodiment, the blood chamber has a spherical configuration during diastole wherein the dome configuration is in the reverse, projecting orientation. This spherical configuration is convertible to a substantially hemispherical configuration 20b as shown in FIG. 3 upon full extension of the first pumping member 12 during systole which displaces the reverse projecting dome 20 of the spherical configuration forward, substantially reducing the interior volume of the blood chamber to pump blood into the circulatory system.

In view of the reduction of pumping chamber volume, a venting port 29 is required unless the second pumping means is applied with counterpulsation as previously discussed.

Figure 4:
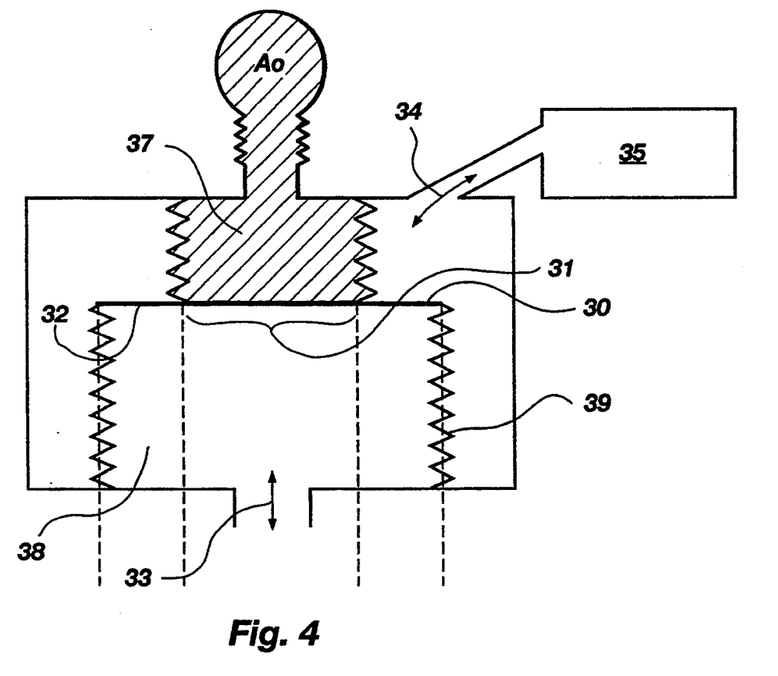
FIG. 4 shows a bellows configuration for the present invention wherein first and second pumping members form a common septum between pumping and blood chambers.

An additional embodiment of the proposed ventricle is shown in FIG. 4 wherein a portion of the second pumping member 30 forms a common septum 31 with a portion of the first pumping member 32, the common septum 31 being displaced in pumping action by the collective forces of the driving force 33 generated by the muscle tissue and the pumping force 34 generated by the second pumping means 35. As with earlier examples, the common septum 31 has a substantially lesser diameter than the diameter of the first pumping member to thereby amplify the drive force generated by the muscle tissue. To facilitate expansion and collapse of the respective chambers of the blood chamber 37 and drive chamber 38, a bellows structure 39 is provided and operates in conventional manner.

Figure 5:
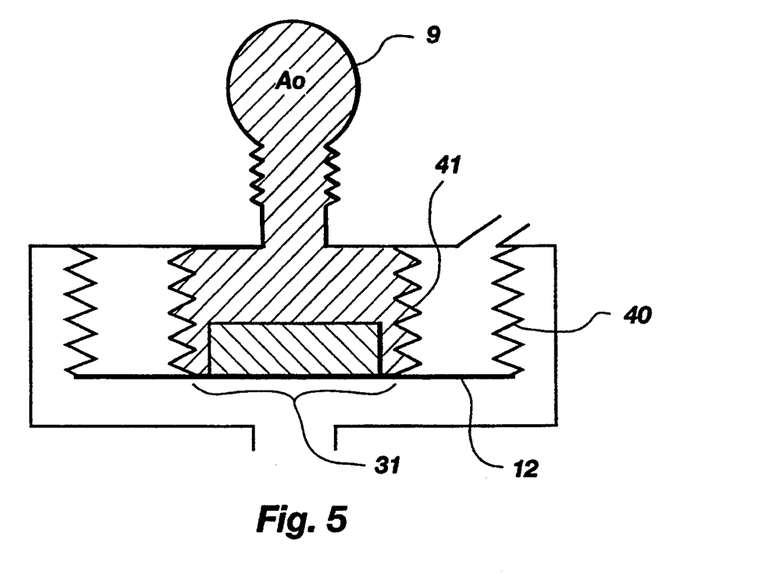
FIG. 5 depicts a second, telescopic embodiment of the configuration shown in FIG. 4.

In this configuration, the respective drive and blood chambers are linearly arranged in nonoverlapping series which requires greater length for the device. FIG. 5 illustrates a telescopic assembly wherein the bellows section 40 of the drive means is linearly overlapping with the blood chamber 41, extending around the blood chamber in a telescopic relationship wherein the blood compartment extends and contracts linearly within a surrounding portion of the drive chamber. This reduces the size to a more compact design for the ventricle.

With respect to material construction of the respective pumping members, the first pumping member generally comprises a first rigid disk which operates to receive the force from the muscle contraction. In FIGS. 1, 2 and 3, the second pumping member comprises a pliable material which is typically used in a collapsible blood sac. In FIGS. 4 and 5, the first and second pumping members are actually part of a single rigid disk. In this sense, both pumping members comprise a rigid disk. As with prior embodiments, the second rigid disk is substantially lesser in diameter than the diameter of the first rigid disk and is coupled to a portion of the blood compartment to apply a direct pumping force to the blood compartment.

Figure 6:
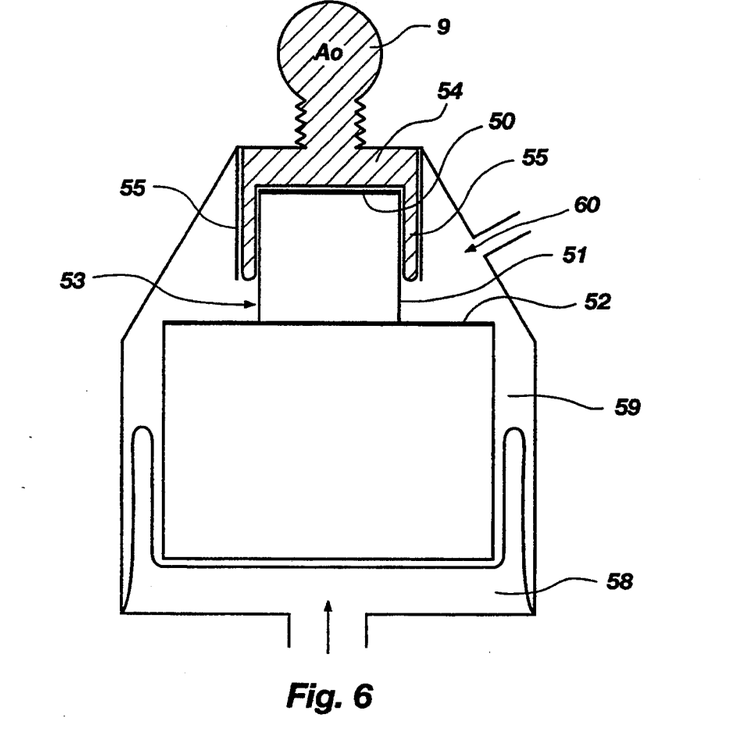
FIG. 6 illustrates an embodiment wherein the second pumping member is formed in a piston configuration as a rigid extension from the first pumping member.

FIG. 6 depicts a modified version of this latter embodiment wherein the second rigid disk 50 is coupled in fixed relationship by support structure 51 to the first rigid disk 52 to form a projecting, rigid extension 53. The blood compartment 54 includes a roll-sock configuration 55 around the projecting, rigid extension 53 of the first rigid pumping member to form a telescopically surrounding volume of the blood compartment in which the projecting, rigid extension 53 operates as a pumping piston with respect to blood contained in the blood compartment. The drive means includes a first pumping chamber 58 which is muscle powered, and a second pumping chamber 59 which is powered by a pneumatic source 60.

Figure 7:
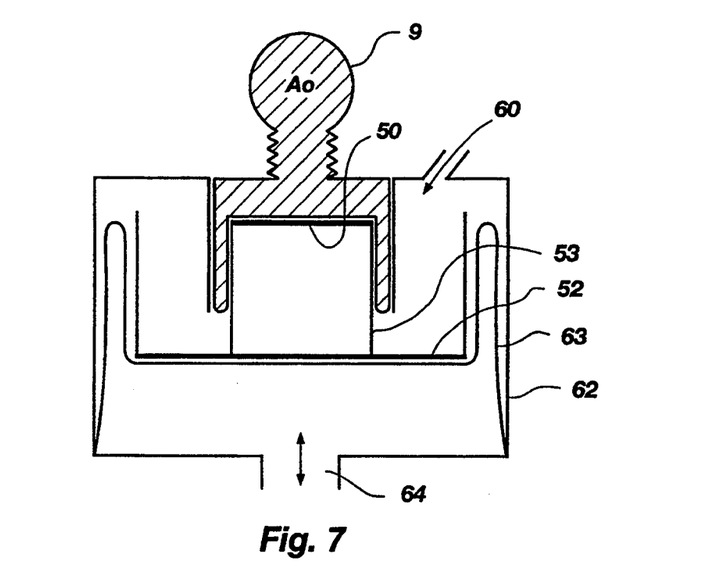
FIG. 7 shows an additional, telescopic form of the device of FIG. 6.

In FIG. 7, the first rigid disk 52 is contained within a housing 62 of fixed volume. The first rigid disk 52 is capable of displacement within the housing and is attached thereto within a surrounding annular, flexible wall 63 which is configured in a roll-sock configuration such that the rigid disk reciprocates in piston-like manner within the surrounding flexible wall 63. The housing includes an inlet port 64 to a compressible means (not shown) which is attached to the housing and supplies the drive force from the muscle contraction.

Figure 8:
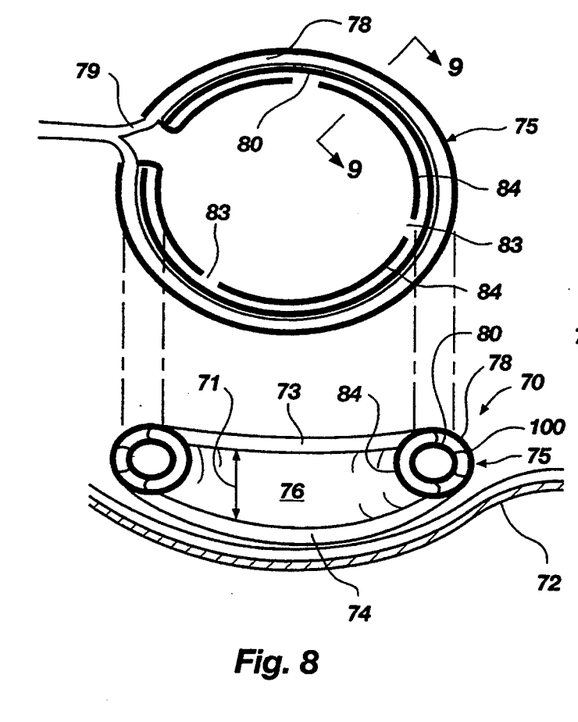
FIG. 8 represents a saucer configuration as an additional embodiment of the present invention.

FIG. 8 is yet another embodiment which adopts a saucer configuration 70 suited for use with muscular contraction 72. The bottom section of this figure shows the side view of the saucer configuration in cross-section. The connecting lines correlate to the same structure rotated to a top view, shown in cross-section through the plane of the saucer. Contraction of this muscle compresses the saucer thickness 71, generating the drive force as noted hereafter. In this embodiment, the compressible means of the drive chamber comprises a pair of opposing flexible diaphragms 73 and 74 sealed at their periphery to opposite sides of a tube member 75. This forms the saucer structure with a saucer interior volume 76 in which the tube member forms an enclosing perimeter for the interior volume sandwiched between the opposing diaphragms 73 and 74. The interior volume provides a reservoir for the drive fluid, which may be gas or liquid.

Figure 9:
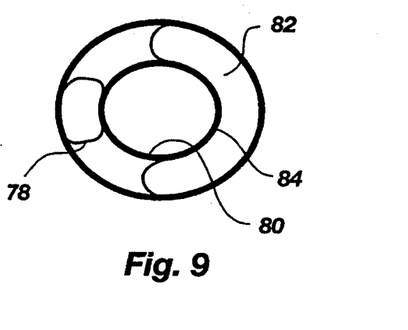
FIG. 9 shows a cross-section of the embodiment shown in FIG. 8, taken along the lines 9—9.

The tube member, as shown more clearly in FIG. 9, includes an outer, collapsible pumping tube 78 which extends around the perimeter of the saucer interior volume and within the tube member. This tube exits the saucer in the form of a conduit 79 which includes means for attachment to the ventricle to supply the drive force to operate the ventricle. The tube member further includes a noncompressible pumping member 80 which is positioned in a common plane and in contact with the collapsible pumping tube. This noncompressible pumping member 80 is substantially larger in diameter, up to approximately twice the diameter of the collapsible pumping tube and includes means to distend within the saucer interior volume and against the collapsible pumping tube to a larger radius in response to increased pressure of the drive fluid within the saucer interior volume. The noncompressible pumping member at least partially collapses the outer pumping tube to generate the drive force within the drive fluid contained in the conduit coupled to the ventricle to pump blood from the blood chamber.

The void space 82 shown in FIG. 9 is filled with pumping fluid through openings 83. As the muscle contracts, increased pressure of the fluid pushes against a resistance wall 84 which is anchored to the top and bottom diaphragms 73 and 74. This causes the compression force to impose against the noncompressible tube 80, extending its radius to partially collapse the pumping tube 78.

Figures 10, 11:
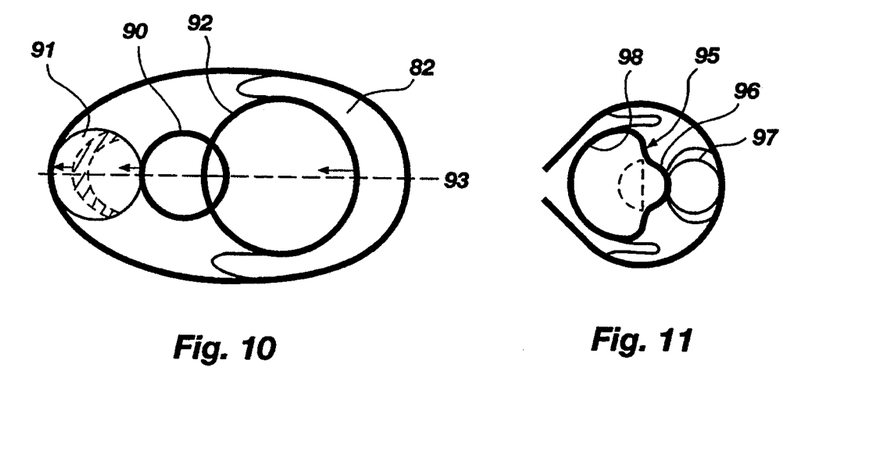
FIG. 10 depicts an additional embodiment of the invention shown in FIG. 8.
FIG. 11 shows a further embodiment of the present invention with a different pumping configuration.

FIG. 10 illustrates how a second noncompressible tube 92 applies the amplification technique discussed above. In this embodiment, the device includes a first noncompressible tube 90 having a diameter approximately equal to the diameter of the collapsible pumping tube 91 and a second noncompressible tube 92 having a diameter substantially larger than the first noncompressible tube. These respective first and second noncompressible tubes are positioned within a common plane 93 with the collapsible pumping tube 91. The first compressible tube is in contact at its outer periphery with an interior perimeter of the collapsible pumping tube. This combination includes means to distend outward the noncompressible tubes outward in response to the drive fluid to collapse the outer pumping tube to generate the drive force within the conduit coupled to the ventricle to pump blood flow from the blood chamber.

It should be noted that the openings 83 and resistance wall 84 are also applied with respect to this additional embodiment of FIG. 10. This sealing structure 84 with its openings 83 also serves as a damping barrier proximate to an interior perimeter of the second noncompressible tube 92. From this perspective, this resistance or sealing wall defines a narrow flow channel 82 between the barrier and the second noncompressible tube for enabling flow of drive fluid therein in response to pumping action of the muscle tissue at the opposing diaphragms. The openings 83 dampen fluid transfer between the saucer interior volume and the narrow flow channel of the barrier to apply drive force to the second noncompressible tube.

FIG. 11 shows yet another embodiment of a saucer type configuration for the pumping device. In this case, the noncompressible member 95 comprises a first noncompressible axial half tube section 96 having a diameter approximately equal to the diameter of the collapsible pumping tube 97. The remaining noncompressible tube section 98 completes the full tubular body and has a diameter substantially larger than the first noncompressible half tube section. The respective first and remaining noncompressible tubes are positioned within a common plane with the collapsible pumping tube 97 with the first noncompressible tube half section 96 being in contact at its outer periphery with an interior perimeter of the collapsible pumping tube 97. Hereagain, the respective first and remaining noncompressible tubes include means to distend outward in response to the drive fluid to collapse the outer pumping tube to generate the drive force within the conduit coupled to the ventricle to pump blood flow from the blood chamber.

Figure 12:
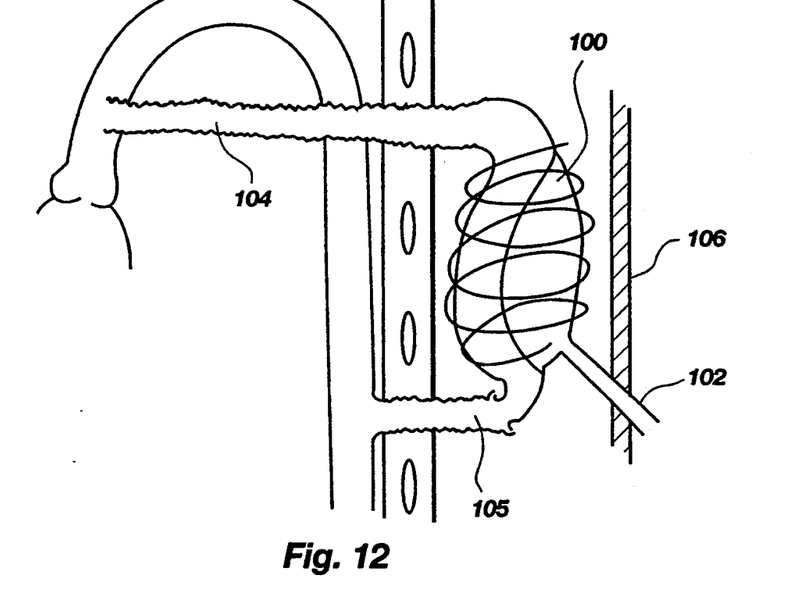
FIG. 12 shows an additional embodiment with a bifurcated feed system as a left ventricular assist device.
Figure 13:
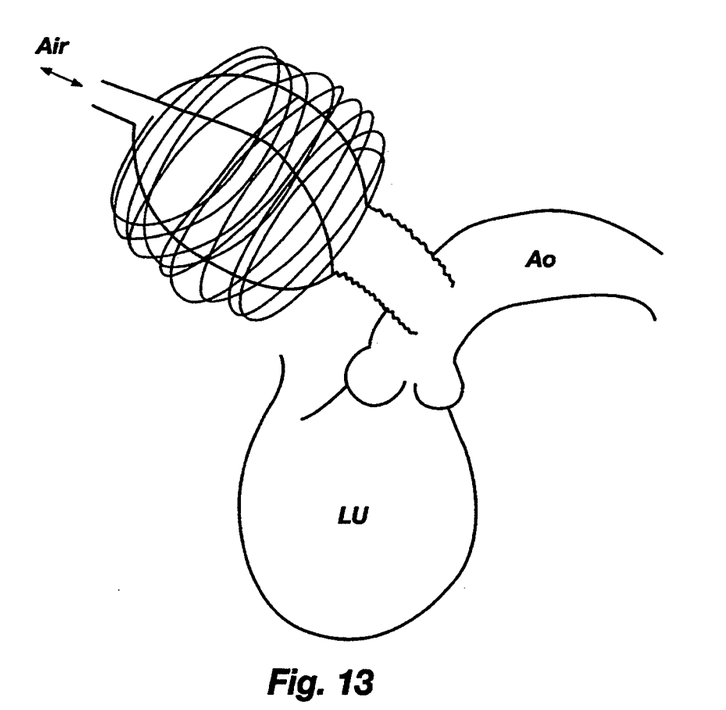
FIG. 13 shows a simple form of skeletal muscle activated blood pump connected to the aorta for counterpulsation. The blood pump is provided with a membrane. The space under said membrane can be used as a pump with air, gas or fluid.

It will be apparent to those skilled in the art that the various embodiments disclosed herein are merely exemplary of the inventive principles and should not be considered limiting on the claim language that follows. In addition to structural variations to the ventricle, FIG. 12 shows how a bifurcated or double-ended connecting conduit can be used to supply blood at two separate locations of the aorta. In this instance the ventricle 100 includes its surrounding muscle 101 which supplies power to pump the blood. The supplemental, second pumping means can be supplied through a transdermal air tube 102 to power the ventricle while the muscle is being trained. Two conduits 104 and 105 provide blood to the aorta in response to the pumping action of the ventricle. The air tube 102 can be terminated below the skin 106 after training to provide ready access for pneumatic support if needed. FIG. 12 shows how the blood can be taken back and forth from the aorta. It should be evident to those skilled in the art that the blood can also be taken from the atrium of the patient and can be returned to the aorta; in which case, the tubes should be provided with one-way valves.

Procedures for implanting such a muscle power ventricle are generally described as follows. The chest of the patient is opened. The blood pump as disclosed in the various embodiment above is connected at the root of the aorta at either one or more connecting conduits. The patient is now supported with a pneumatic blood pump and is being maintained by a mechanical drive system.

Training of the muscle is in accordance with techniques as used previously with other myoplastic systems. The pouch is filled with air at approximately 100 mm Hg. The wrapped muscle will initially be only slightly distended because of the aortic pressure within the pouch or blood chamber. The muscle is then trained by counterpulsation at rates of 1 to 2 or 1 to 3. The effect of training is observed by measuring driveline pressures.

Once the muscle is trained, the drive line is stopped and buried under the skin. A peritoneal catheter or other percutaneous device may be used to enable measuring of pressure from time to time, and to replenish gas, which is typically carbon dioxide.

The above devices and techniques may be represented in a general methodology of the present invention as follows. Ventricular assist to a patient with a weak or nonfunctional heart, may be applied in the following steps. The attending physician begins by attaching an artificial ventricle to the patient in a ventricular assist location. The ventricle is pumped with a muscled powered pump which supplies a driving force to pump blood from the artificial ventricle to the patient. This pumping action is supplemented as needed with a pneumatic pumping system that operates with respect to the same ventricle. This methodology may further comprise the step of amplifying the pumping pressure of the muscle powered pump by driving a second pumping member of lesser dimension with a first pumping member of larger dimension, and thereby supplying increased pressure to overcome existing blood pressure in the aorta. It shall be clear to those skilled in the art that the muscle-powered energy source can be located almost any place in the body, activated by one or multiple muscles and connected with conduits to the blood pump.

The various aspects of the disclosed invention are set forth in the accompanying claims.

We claim:

1. A method for providing ventricular assist to a patient with a weak or nonfunctional heart, said method comprising the steps of:

a) attaching an artificial ventricle to the patient in a ventricular assist location;

b) pumping the artificial ventricle with a muscle powered pump which supplies a fluid as a driving force to pump blood from the artificial ventricle to the patient;

c) amplifying pumping pressure of the muscle powered pump by (i) directing the driving force onto a first pumping member having a contacting side of larger dimension; and (ii) directing said contacting side of said first pumping member against a contacting side of smaller dimension of a second pumping member without directing said first pumping member against any other pressure-resistant member to thereby transfer the driving force as increased pressure onto said second pumping member.

2. A method as in claim 1 wherein step (c) further comprises directing a hydraulic force against a portion of the first pumping member, said portion having a larger dimension than that of the entire second pumping member.

3. A method as in claim 1 wherein step (b) further comprises the following steps:

(d) wrapping a compressible hydraulic pumping chamber of the artificial ventricle with a muscle; and (e) stimulating the muscle to expand and contract to thereby alternately compress and release the pumping chamber.

4. A method as in claim 3 wherein the first pumping member is an integral part of the hydraulic pumping chamber and the second pumping member is in integral part of a compressible blood pumping chamber of the artificial ventricle, step (c) further comprising transferring the driving force from the hydraulic pumping chamber onto a blood pumping chamber of the artificial ventricle.

5. A method for providing ventricular assist to a patient with a weak or nonfunctional heart, said method comprising the steps of:

a) attaching an artificial ventricle to the patient in a ventricular assist location;

b) pumping the artificial ventricle with a muscle powered pump which supplies a liquid actuated driving force to pump blood from the artificial ventricle to the patient; and c) supplementing the artificial ventricle as needed with a pneumatic pumping system sealed from the liquid that operates with respect to the same ventricle;

wherein step (b) further comprises directing the driving force to one side of a pumping member having opposing sides, and wherein step (c) further comprises applying a pneumatic pumping force to a side of said pumping member opposite said one side.

6. A method for providing ventricular assist to a patient with a weak or nonfunctional heart, said method comprising the steps of:

a) attaching an artificial ventricle to the patient in a ventricular assist location;

b) pumping the artificial ventricle with a muscle powered pump which supplies a liquid actuated driving force to pump blood from the artificial ventricle to the patient; and c) supplementing the artificial ventricle as needed with a pneumatic pumping system sealed from the liquid that operates with respect to the same ventricle;

wherein step (c) further comprises pumping the pneumatic pumping system in counterpulsation to the liquid actuated driving force.

* * * * *